US006100047A

United States Patent [19]
Wilkison et al.

[11] Patent Number: 6,100,047
[45] Date of Patent: Aug. 8, 2000

[54] MODULATION OF THE SULFONYLUREA RECEPTOR AND CALCIUM IN ADIPOCYTES FOR TREATMENT OF OBESITY/DIABETES

[75] Inventors: William O. Wilkison, Bahama, N.C.; Michael B. Zemel; Naima Moustaid-Mousse, both of Knoxville, Tenn.

[73] Assignees: Zen Bio, Inc., Research Triangle Park, N.C.; The University of Tennessee Research Corporation, Knoxville, Tenn.

[21] Appl. No.: 09/287,907

[22] Filed: Apr. 7, 1999

Related U.S. Application Data
[60] Provisional application No. 60/081,189, Apr. 8, 1998.
[51] Int. Cl.$^7$ ........................ G01N 33/566; G01N 33/567
[52] U.S. Cl. ............................ 435/7.2; 435/7.21; 435/7.1
[58] Field of Search ........................... 435/7.1, 7.2, 7.21; 514/866, 909; 436/71

[56] References Cited

PUBLICATIONS

Byyny et al. "Cytosolic Calcium and Insulin Resistance in Elderly Patients With Essential Hypertension", *American Journal of Hypertension* 5(7):459–464. (Jul. 1992).
Zemel "Insulin Resistance, Obesity and Hypertension: An Overview",*J. Nutr.* 125(6S):1715S–1717S. (Apr. 1994).
Zemel "Insulin Resistance vs. Hyperinsulinemia in Hypertension: Insulin Regulation of $Ca^{2+}$ Transport and $Ca^{2+}$ —Regulation of Insulin Sensitivity", *J. Nutr.* 125(6S):1738S–1743S. (Apr. 1994).
Kim et al. "Agouti Regulation of Intracellular Calcium: Role of Melanocortin Receptors",*Am J Physiol* 272(3 Pt 1):E379–84. (Mar. 1997).
Zemel et al. "Agouti Regulation of Intracellular Calcium: Role in the Insulin Resistane of Viable Yellow Mice", *Proc. Natl. Acad. Sci. USA* 92:4733–4737. (May 1995).
Jones et al. (1996) "Upregulation of Adipocyte Metabolism by Agouti Protein: Possible Paracrine Actions in Yellow Mouse Obesity", *Am. J. Physiol.* 270E192–E196.
Xue et al. (Oct. 1998) "The Agouti Gene Product Inhibits Lipolysis in Human Adipocytes Via a $Ca^{2+}$—Dependent Mechanism", *FASEB J.* 12:1391–1396.
Abel et al. "Impaired Recovery of Vascular Smooth Muscle Intracellular Calcium Following Agonist Stimulation in Insulin Resistant (Zucker Obese) Rats", *American Journal of Hypertension* 6(6 Pt 1):500–504. (Jun. 1993).
Zemel et al. "Hypertension in Insulin–Resistant Zucker Obese Rats is Independent of Sympathetic Neural Support", *American Journal of Physiology* 262(3 Pt 1):E368–E371. (Mar. 1992).
Aguilar–Bryan et al. (1995) "Cloning of the β Cell High–Affinity Sulfonylurea Receptor: A Regulator of Insulin Secretion", *Science* 268:423–426.
Alemzadeh et al. (1993) "Modification of Insulin Resistance by Diazoxide in Obese Zucker Rats", *Endocrinology* 133(2):705–712.

Alemzadeh et al. (1996) "Antiobesity Effect of Diazoxide in Obese Zucker Rats", *Metabolism* 45(4):334–341.
Alemzadeh et al. (Jun. 1998) "Beneficial Effect of OBESe Hyperinsulinemic Adults",*J. Clin. Endocr. Met.* 83(6):1911–1915.
Moustaid et al. (1996) "Insulin Increases Lipogenic Enzyme Activity in Human Adipocytes in Primary Culture", *J. Nutr.* 126:865–870.
Jones et al. (1997) "Angiotensin II Increases Lipogenesis in 3T3–L1 and Human Adipose Cells", *Endocrinology* 138(4):1512–1519.
Draznin et al. (1987) "Insulin and Glyburide Increase Cytosolic Free–$Ca^{2+}$ Concentration in Isolated Rat Adipocytes", *Diabetes* 36:174–178.
Michaud et al. "Obesity and the Adipocyte", *Journal of Endocrinology* 155(2):207–209. (Nov. 1997).
Ambrozy et al. "Effects of Dietary Calcium on Blood Pressure, Vascular Reactivity and Vascular Smooth Muscle Calcium Efflux Rate in Zucker Rats", *American Journal of Hypertension* 4(7 Pt 1):592–596. (Jul. 1991).
Mynatt et al. "Combined Effects of Insulin Treatment and Adipose Tissue–Specific Agouti Expression on the Development of Obesity", *Proc. Natl. Acad. Sci. USA* 94(3):919–922. (Apr. 1997).
Sowers et al. "Insulin Resistance, Carbohydrate Metabolism, and Hypertension",*American Journal of Hypertension* 4(7 Pt 2):466S–472S. (Jul. 1991).
Zemel et al. "Insulin Attenuation of Vasoconstrictor Responses to Phenylephrine in Zucker Lean and Obese Rats", *American Journal of Hypertension* 4(6):537–539. (Jun. 1991).
Kim et al. "The Effects of Calcium Channel Blockade on Agouti–Induced Obesity", *The FASEB Journal* 10(14):1646–1652. (Dec. 1996).

(List continued on next page.)

*Primary Examiner*—Marjorie Moran
*Attorney, Agent, or Firm*—Alston & Bird LLP

[57] ABSTRACT

The invention provides methods for identifying compounds and compositions useful in the regulation of weight, the treatment of obesity, diabetes and other insulin resistance-related disorders hypertension, cardiovascular disease and the like. The methods comprise the use of adipocytes and predipocytes in assays and screens for compounds or compositions of interest. The present invention recognizes the presence of the sulfonylurea receptor in adipocytes and its utility in identifying compounds and in treating obesity and other insulin resistance-related disorders. The methods of the invention also provide for identifying novel calcium channels or other calcium regulatory channels that are selectively expressed in human adipocytes as compared to human preadipocytes and for screening adipocytes for compounds that selectively antagonize calcium. These compounds may be used in the treatment of obesity and diabetes and other insulin resistance-related disorders. Once identified, the compounds of the invention can be used in pharmaceutical compositions for the treatment of insulin resistance-related disorders and to regulate lipogenesis and lipolysis.

8 Claims, 3 Drawing Sheets

OTHER PUBLICATIONS

Thomas et al. "Mutations in the Sulfonylurea Receptor Gene in Familial Persistent Hyperinsulinemic Hypoglycemia of Infancy", *Science* 268:426–429. (Apr. 1995).

Jacobs et al. "Sulfonylurea Potentiates Insulin–Induced Recruitment of Glucose Transport Carrier in Rat Adipocytes",*J. Biol. Chem.* 260(5):2593–2596. (Mar. 1985).

Martz et al. "Sulfonylurea Binding to Adipocyte Membranes and Potentiation of Insulin–Stimulated Hexose Transport",*J. Biol Chem.* 264(23):13672–13678. (Aug. 1989).

Muller et al. (1996) "Characterization of the Molecular Mode of Action of the Sulfonylurea, Glimepiride, at Adipocytes",*Horm. Metab. Res.* 28:469–487.

Muller et al. (1994) "Stimulation of Glucose Utilization in 3T3 Adipocytes and Rat Diaphragm In Vitro By the Sulphonylureas, Glimepiride and Glibenclamide, is Correlated with Modulaitons of the cAMP Regulatory Cascade",*Biochem. Pharmacol.* 48(5):985–996.

Inagaki et al. "Reconstitution of $I_{KATP}$: An Inward Rectifier Subunit Plus the Sulfonylurea Receptor", *Science* 270:1166–1170. (Nov. 1995).

Draznin et al. "Possible Role of Cytosolic Free Calicum Concentrations in Mediating Insulin Resistance of Obesity and Hyperinsulinemia", *The Journal of Clinical Investigation* 82(6):1848–1852. (Dec. 1988).

Lehmann et al. "An Antidiabetic Thiazolidinedione Is a High Affinity Ligand for Peroxisome Proliferator–activated Receptor γ (PPARγ)",*J. Biol. Chem.* 270(22):12953–12956. (Feb. 1996).

Draznin et al. "The Existence of an Optimal Range of Cytosolic Free Calcium for Insulin–Stimulated Glucose Transport in Rat Adipocytes",*The Journal of Biological Chemistry* 262(30):14385–14388. (Oct. 1987).

Sturgess et al. (Aug. 31, 1985) "The Sulphonylurea Receptor May Be An ATP–Sensitive Potassium Channel", *The Lancet vol. II*, No. 8453:474–475.

Kwon et al. "Molecular Structure and Chromosomal Mapping of the Human Homolog of the Agouti Gene",*Proc. Natl. Acad. Sci. USA* 91(21):9760–9764. (Oct. 1994).

Bokvist et al. "Separate Processes Mediate Nucleotide–Induced Inhibition and Stimulation of the ATP–Regulated $K^+$–Channels in Mouse Pancreatic β–Cells", *Proc. R. Soc. Lond.* 243(1307):139–144. (Feb. 1991).

Gilon et al. "Oscillations of Secretion Driven by Oscillations of Cytoplasmic $Ca^{2+}$ as Evidenced in Single Pancreatic Islets", *The Journal of Biological Chemistry* 268(30):22265–22268. (Oct. 1993).

Philipson "ATP–Sensitive $K^+$ Channels: Paradigm Lost, Paradigm Regained", *Science* 270:1159. (Nov. 1995).

Pérusse et al. (Jan. 1999) "The Human Obesity Gene Map: The 1998 Update", *Obesity Research* 7(1):111–129.

Hani et al. (1997) "Genetic Studies of the Sulfonylurea Receptor Gene Locus in NIDDM and in Morbid Obesity Among French Caucasians", *Diabetes* 46(4):688–694.

Rajan et al. (1994) "Do Adipocytes Contain High Affinity Sulfonylurea Receptors?", *Endocrinology* 134(3):1581–1588.

Maloff et al. "In Vitro Effects of a Sulfonylurea on Insulin Action in Adipocytes",*J. Clin Invest.* 68:85–90. (Jul. 1981).

MODULATION OF THE SULFONYLUREA RECEPTOR AND CALCIUM IN ADIPOCYTES FOR TREATMENT OF OBESITY/DIABETES

CROSS-REFERENCE TO RELATED APPLICATION

This application claims the benefit of U.S. Provisional Application No. 60/081,189, filed on Apr. 8, 1998.

FIELD OF THE INVENTION

This invention relates to methods of identification of the sulfonylurea receptor in human adipocytes and other adipocyte-selective calcium channels and calcium mobilization antagonists and use of these factors for treatment of obesity, diabetes, and insulin-resistance related syndromes.

BACKGROUND OF THE INVENTION

Mice with dominant mutations at the agouti locus, including lethal yellow ($A^y$) and viable yellow ($A^{vy}$) are characterized by obesity, insulin resistance, and yellow coat color. The mouse agouti gene normally regulates differential pigment production in hair-bulb melanocytes. Each melanocyte in the hair bulb switches between the production of eumelanin (black) and phaeomelanin (yellow), producing the wild-type mouse coat color of a black hair with a subapical band of yellow. Agouti mutations disrupt this switching process and form a dominance hierarchy in which the dominant alleles produce a yellow coat and the recessive alleles produce a black coat.

Although agouti is normally expressed in neonatal skin, dominant agouti mutations are characterized by ectopic overexpression of agouti throughout life. This is due to mutations in the promoter/regulatory region rather than in protein-coding domain. Transgenic mice designed to express the agouti coding portion in a ubiquitous manner also develop a syndrome of obesity, hyperinsulinemia, hyperglycemia and yellow coat color, similar to $A^{vy}$ mutation, demonstrating that ectopic overexpression of the agouti gene is directly responsible for pleiotropic effects associated with dominant agouti mutations. However, the mechanism linking this pigmentation gene to obesity has not yet been identified.

There is needed methods for the identification of compositions and compounds for the treatment and control of insulin resistance-related disorders.

SUMMARY OF THE INVENTION

The invention provides methods for identifying compounds and compositions useful in the regulation of weight, the treatment of obesity, diabetes and other insulin resistance-related disorders hypertension, cardiovascular disease and the like. The methods comprise the use of adipocytes and predipocytes in assays and screens for compounds or compositions of interest. The present invention recognizes the presence of the sulfonylurea receptor in adipocytes and its utility in identifying compounds and in treating obesity and other insulin resistance-related disorders.

In addition to assaying for agonists and antagonists of the sulfonylurea receptor, the methods of the invention also provide for identifying novel calcium channels or other calcium regulatory channels that are selectively expressed in human adipocytes as compared to human preadipocytes and for screening adipocytes for compounds that selectively antagonize calcium. These compounds may be used in the treatment of obesity and diabetes and other insulin resistance-related disorders.

Once identified, the compounds of the invention can be used in pharmaceutical compositions for the treatment of insulin resistance-related disorders and to regulate lipogenesis and lipolysis.

A. Addition of 20 M glibenclamide results in an increase in intracellular calcium. Glibenclamide (Glib) was added at time designated by the arrow. B. The dose-responsive effect of glibenclamide on $[Ca^{2+}]_i$ in human adipocytes. Glibenclamide was added at 10 and 20 M at the indicated times. * $p<0.05$ vs. Control, ** $p<0.05$ vs. 10 $\mu$M glibenclamide.

Figure 3A:
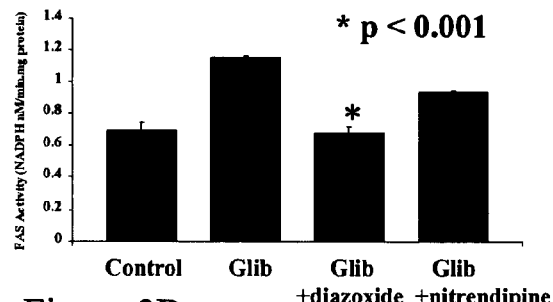
Figure 3B:
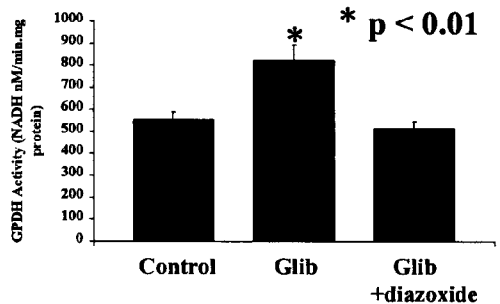

FIG. 3. The lipogenic effect of glibenclamide in human adipocytes. As an indicator of lipogenic stimulation, both FAS and GPDH activity were measured. A. Glibenclamide stimulation of FAS activity. Human adipocytes were treated with 10 $\mu$M glibenclamide alone, 10 $\mu$M glibenclamide plus 10 $\mu$M diazoxide or 10 $\mu$M glibenclamide plus 30 nM nitrendipine for 48 hr. FAS was measured as described (6, 14). * $p<0.001$ vs. Control. B. Glibenclamide stimulation of GPDH activity. Human adipocytes were treated with 10 $\mu$M glibenclamide or 10 $\mu$M glibenclamide plus 10 $\mu$M diazoxide for 48 hr. GPDH activity was measured as described (14). * $p<0.01$ vs. Control.

Figure 4:
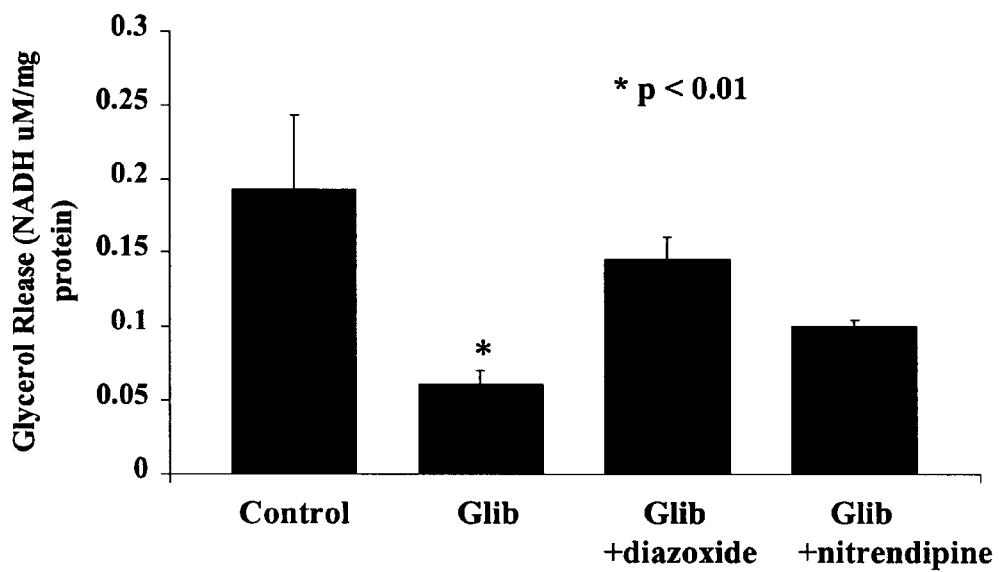

FIG. 4. The anti-lipolytic effect of glibenclamide in human adipocytes. Activation of lipolysis in adipocytes is typically measured by release of glycerol into the media. Human adipocytes were treated with 10 $\mu$M glibenclamide alone, 10 $\mu$M glibenclamide plus 10 $\mu$M diazoxide or 10 $\mu$M glibenclamide plus 30 $\mu$M nitrendipine for 48 hr. Glycerol release was determined as described (19). * $p<0.01$ vs. Control.

Figure 2A:
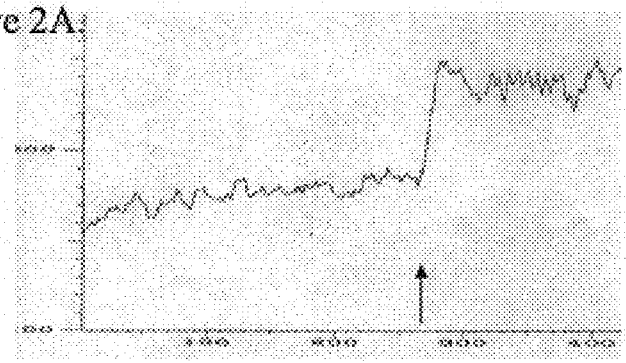
FIG. 2. Glibenclamide stimulation of $[Ca^{2+}]_i$ in isolated human adipocyte. $[Ca^{2+}]_i$ in isolated human adipocytes was determined fluorometrically as previously described (4,7). Briefly, the human adipocytes isolated as described above were incubated in DMEM medium overnight for cell recovery. Prior to $[Ca^{2+}]_i$ measurement, adipocytes were pre-incubated in serum-free medium for 2 hrs, rinsed with HBSS solution containing the following components in mM: NaCl 138, $CaCl_2$ 1.8, $MgSO_4$ 0.8, $NaH_2PO_4$ 0.9, $NaHCO_3$ 4, glucose 20, glutamine 6, HEPES 20 and BSA 1%. Cells were then loaded with fura-2 acetoxymethyl ester (10 μM) in the same buffer for 45 min at 37° C. in the dark with continuous shaking. To remove extracellular dye, cells were rinsed with HBSS for 3 times and resuspended in this solution at a concentration of $2 \times 10^5$ cells/ml. $[Ca^{2+}]_i$ was measured using dual excitation (340 and 380 nm) and single emission (510 nm) fluorometry. Following the establishment of stable baseline, the response to glibenclamide (10 and 20 μM) was determined. Digitonin (25 μM) and Tris/EGTA (100 mM) were used to measure maximal and minimal fluorescence to calibrate the signals, and final $[Ca^{2+}]_i$ was then calculated by the equation of Grynkiewicz et al. (17).
Figure 2B:
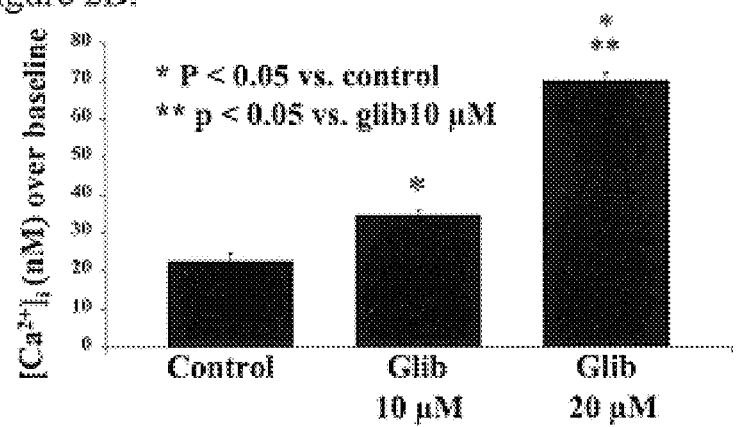
Figure 5:
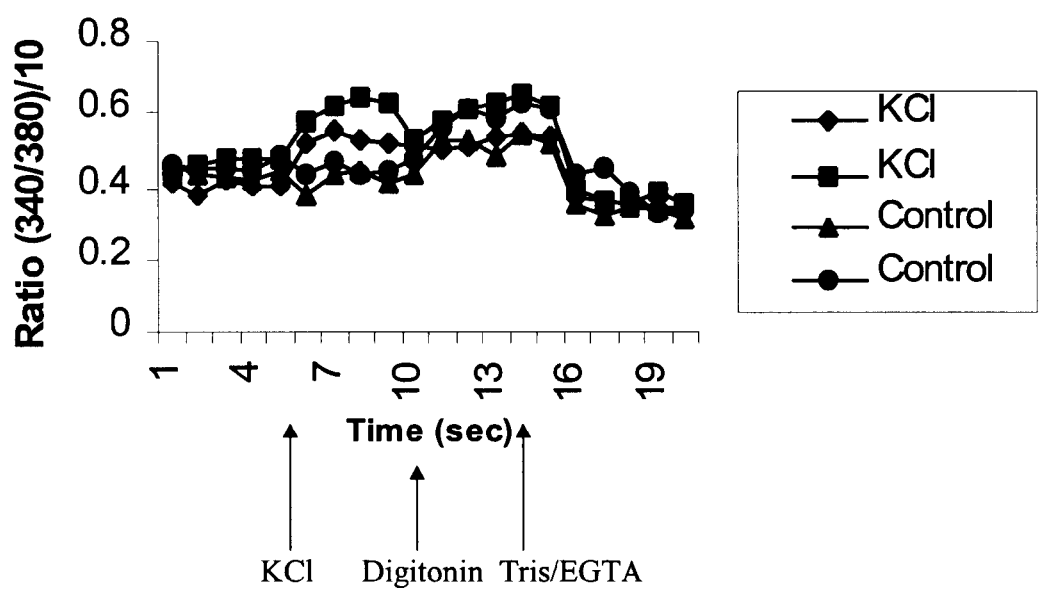

FIG. 5. Multiplate well assay for the screening of compounds increasing $[Ca^{2+}]_i$ in human adipocytes. Adipocytes were prepared in a 96-well plate and loaded with fura-2-AM, 10 $\mu$M as described for FIG. 2. All measurements were made in a Packard Fluorocount system using excitation filters of 340 and 380 nm and emission filter of 510 nm. The 340/380 ratio is proportional to $[Ca^{2+}]_i$. The data shown represents four wells of a 96-well adipocyte plate. The data sets depicted by squares and diamonds received a pulse of KCl to stimulate $Ca^{2+}$ influx, while the data sets depicted by circles and triangles received a pulse of vehicle at 5 seconds. At 10 seconds, all preparations are given a pulse of digitonin (25 $\mu$M), which resulted in an expected increase in $Ca^{2+}$ in all preparations, and at 14 seconds all preparations were given a pulse of pH 8.7 Tris/EGTA which results in a predictable decrease in $[Ca^{2+}]_i$.

DETAILED DESCRIPTION OF THE INVENTION

Methods are provided for the identification of compounds and compositions useful in the treatment of insulin resistance-related disorders. The methods of the invention use adipocytes and predipocytes in such assay methods. The method of the invention herein provides for the identification of a functional sulfonylurea receptor in adipocytes. The sulfonylurea receptor can be used to screen for agonists and antagonists of the receptor. The compounds find use in the treatment of obesity and diabetes. This method also provides for the method of identification of calcium channels or other calcium regulatory channels such as potassium ATP channels that are selective for human adipose tissue and/or human adipocytes. In particular, this method includes the production of human cultured adipocyte, isolation of human primary adipocytes, preparation of mRNA and/or cDNA libraries of said cells, and PCR cloning of novel channel/receptor cDNAs.

The invention provides for the establishment of a calcium mobilization assay using human cultured adipocytes to identify novel molecules that antagonize calcium mobilization in these cells. These assays may take several forms but are generally modeled after use of a calcium responsive fluorescent dye (such as Fura-2). The adipocytes will be plated in multiwell or coverslip formats to accommodate the method of assay. The invention also provides for methods to allow identification of adipocyte-selective molecules.

The invention also provides for the evaluation of these selective molecules in relevant obesity and diabetes animal models to determine the relevance of these molecules in treating human obesity and diabetes and insulin resistance-related disorders.

"Insulin resistance-related disorders" include obesity, diabetes, cardiac disorders, weight regulation disorders, eating disorders, anorexia, cachexia, and the like.

Thus, in one aspect, the invention provides a method of determining the ability of a compound to act as a SUR1 antagonist, comprising:
  (a) incubating cultured adipocytes in the presence and absence of said compound, and
  (b) comparing the level of at least one lipogenic or anti-lipolytic marker in said adipocytes after incubation in the presence and absence of said compound.

The cultured adipocytes may be derived from any animal. Preferably the adipocytes are mammalian. More preferably the adipocytes are rodent or primate. Most preferably the adipocytes are human.

Any lipogenic or anti-lipolytic marker may be assayed in the methods of the invention. Assays for such markers are know to those skilled in the art. Particularly useful lipogenic markers are $Ca^{2+}$ influx, FAS activity, GPDH activity and triglyceride accumulation. Particularly useful anti-lipolytic markers are glycerol release into the culture medium and increased intracellular cAMP levels.

In another aspect, the invention provides a method of determining the ability of a compound to regulate lipogenesis or lipolysis, comprising:
  (a) incubating cultured adipocytes in the presence and absence of said compound, and
  (b) comparing the level of at least one lipogenic or anti-lipolytic marker in said adipocytes after incubation in the presence and absence of said compound.

In yet another aspect, the invention provides a method of determining the ability of a compound to modulate obesity, diabetes, hypertension or other cardiovascular disease, comprising:
  (a) incubating cultured adipocytes in the presence and absence of said compound, and
  (b) comparing the level of at least one lipogenic or anti-lipolytic marker in said adipocytes after incubation in the presence and absence of said compound.

In still another aspect, the invention provides a method of determining the ability of a compound to act as a potassium channel activator, comprising:
  (a) incubating cultured adipocytes in the presence and absence of said compound, and
  (b) comparing the level of at least one lipogenic or anti-lipolytic marker in said adipocytes after incubation in the presence and absence of said compound.

In a variation of the above method, the cultured adipocytes are incubated with a SUR1 agonist in the presence and absence of said compound.

The invention further provides a method to determine the ability of a compound to act as a calcium channel antagonist, comprising:
  (a) incubating cultured adipocytes in the presence and absence of said compound, and (b) comparing the level of at least one lipogenic or anti-lipolytic marker in said and adipocytes after incubation in the presence and absence of said compound.

In a further aspect, the invention provides a method of determining the ability of a compound to act as an adipocyte specific SUR1 antagonist, comprising:

(a) incubating cultured preadipocytes and cultured adipocytes in the presence and absence of said compound, and (b) comparing the level of at least one lipogenic or anti-lipolytic marker in said preadipocytes and adipocytes after incubation in the presence and absence of said compound.

The compounds and compositions of the invention include small molecules, large molecules, or mixtures thereof, peptides, polypeptides, antibodies, nucleotide sequences to control SUR gene expression including increasing or decreasing expression. Antisense molecules can be used to decrease expression and regulatory sequences can be used to design genes for increased expression.

The assays or biological screens of the invention provides a means for identifying and characterizing compounds that are agonists or antagonists of the sulfonylurea receptor, compounds that modulate intracellular calcium flux. The assays utilize adipocyte or preadipocyte cells. Thus, the methods of the invention allow for the identification of compounds using such cells for the treatment of insulin resistance-related disorders. Compositions and methods of the invention are also useful for the modulation of lipogenesis and lipolysis.

The compounds may be formulated into pharmaceutical compositions for administration. Such pharmaceutical compositions of the invention may include one or more protease inhibitors. An exemplary protease inhibitor is sodium pentosan polysulfate (PPS), a polysulfated polysaccharide.

The compositions of the invention may optionally include stabilizing agents including, but not limited to, amino acids (such as arginine, lysine, and glycine), sugars (such as sucrose, mannitol, and trehalose), salts (such as NaCl and $MgCl_2$), surfactants, PEG, preservatives, antimicrobial agents, complexing agents (such as EDTA), and antioxidants.

Preferably, the pharmaceutical composition is isotonic with the cells of the subject. Preferably the pharmaceutical composition is isotonic with the erythrocytes of a subject. More preferably, the pharmaceutical composition is isotonic with human erythrocytes. Thus, in one embodiment, the pharmaceutical composition contains a sufficient concentration of at least on tonicifying agent such that the composition is isotonic.

By "isotonic" is meant a solution in which a cell will neither shrink nor swell. An example of an isotonic solution is 0.9% sodium chloride in water. Typically, an isotonic solution will have about the same osmotic pressure as the fluid phase of a subject's cells or tissue. However, a solution that is isosmotic with intracellular fluid will not be isotonic if it contains a solute that freely permeates cell membranes. To determine is a solution is isotonic, it is necessary to identify the concentration of solutes at which cells will retain their normal size and shape. Methods of determining the isotonicity of a solution are known to those skilled in the art. See, for example, Setnikar et al. (1959) *JAPhA Sci Ed* 48:628.

Those skilled in the art are familiar with a variety of pharmaceutically acceptable solutes useful in providing isotonicity in pharmaceutical compositions. Thus, the compositions of the invention further encompass components that can be used to provide isotonicity, for example, sodium chloride, glycine, mannitol, glycerol, sucrose, and other carbohydrates, acetic acid, other organic acids or their salts, and relatively minor amounts of citrates or phosphates. The ordinary skilled person would know of additional agents that are suitable for providing optimal tonicity.

The pharmaceutical composition can be formulated as a solution, suspension, or emulsion. It can also be in the form of lyophilized powder, which can be converted into solution, suspension, or emulsion before administration. Storage can also be facilitated by adding proteins such as human albumin that can reduce the loss of activity of the pharmaceutically active protein. Thus, albumin could function as a stabilizing protein during the freeze-drying process. The methods for formulating a pharmaceutical composition are generally known in the art. A thorough discussion of formulation and selection of pharmaceutically acceptable carriers, stabilizers, and isomolytes can be found in *Remington's Pharmaceutical Sciences* (1990) ($18^{th}$ ed., Mack Pub. Co., Eaton, Pa.), herein incorporated by reference.

The pharmaceutically active agent can also be formulated in a sustained-release form to prolong the presence of the pharmaceutically active agent in the treated mammal, generally for longer than one day. Many methods of preparation of a sustained-release formulation are known in the art and are disclosed in *Remington's Pharmaceutical Sciences* (1990) ($18^{th}$ ed., Mack Pub. Co., Eaton, Pa., herein incorporated by reference. Generally, the agent can be entrapped in semipermeable matrices of solid hydrophobic polymers. The matrices can be shaped into films or microcapsules.

Examples of such matrices include, but are not limited to, polyesters, copolymers of L-glutamic acid and gamma ethyl-L-glutamate (Sidman et al. (1983) *Biopolymers* 22:547–556), polyactides (U.S. Pat. No. 3,773,919 and EP 58,481), polyactate polyglycolate (PLGA), hydrogels (see, for example, Langer et al. (1981) *J. Biomed. Mater. Res.* 15:167–277; Langer (1982) *Chem. Tech.* 12:98–105), nondegradable ethylene-vinyl acetate, degradable lactic acid-glycolic acid copolyers such as the Lupron Depot®, and poly-D-(—)-3-hydroxybutyric acid (EP 133,988). Suitable microcapsules can also include hydroxymethyl cellulose or gelatin-microcapsules and poly-methylmethacylate microcapsules prepared by coacervation techniques or by interfacial polymerization. In addition, micro emulsions or colloidal drug delivery systems such as liposomes and albumin microspheres, may also be used. See *Remington's Pharmaceutical Sciences* (1990) ($18^{th}$ ed., Mack Pub. Co., Eaton, Pa.).

The compositions of the invention, comprising a pharmaceutically active agent and a succinate compound, can be stored for extended periods of time while maintaining the physical and biological integrity of the pharmaceutically active agent. Storage can be in liquid form or as a dried formulation, which can be reconstituted by adding liquid. When pharmaceutically active agents are proteins, storage can be facilitated by drying processes, such as lyophilization. Accordingly, the protein can be stored in the form of a freeze-dried composition. Thus, in one embodiment, the invention provides a lyophilized pharmaceutical composition comprising a succinate compound and a pharmaceutically active agent.

The pharmaceutical composition is preferably sterilized by membrane filtration and is stored in unit-dose or multi-dose containers such as sealed vials or ampules. In one embodiment of the invention, the head space of the vials can be flushed with nitrogen when filling. The invention also encompasses devices for dosing convenience, such as prefilled syringes, autoinjectors, blister packs, or needleless systems, to make the administration or injection easier.

A pharmaceutically effective amount of the composition of the invention is administered to a subject. By pharmaceutically effective amount is meant an amount that is useful in the treatment, prevention or diagnosis of a disease or condition.

By the term "administer" is intended any suitable method for delivering a pharmaceutically active agent to a subject, including parenteral, intranasal, intrapulmonar, oral, topical, anal or surgical implantation or insertion. Typical parenteral routes of administration include, but are not limited to, intravenous, intramuscular, subcutaneous, intraarterial and intraperitoneal injection or infusion. Preferably the administration is by injection. In preferred embodiments, injection is subcutaneous. Injectable forms of the compositions of the invention include, but are not limited to, solutions, suspensions and emulsions.

By "subject" is intended any animal. Preferably the subject is mammalian, must preferably the subject is human. Mammals of particular importance other than human include, but are not limited to, dogs, cats, cows, horses, sheep and pigs.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The pharmaceutical composition may be formulated in a unit dosage and in an injectable or infusible form such as solution, suspension, or emulsion. It can also be in the form of lyophilized powder, which can be converted into solution, suspension, or emulsion before administration. The pharmaceutical composition is preferably sterilized by membrane filtration and is stored in unit-dose or multi-dose containers such as sealed vials or ampules.

The compositions of the invention may be formulated with pharmaceutical carriers. Such carriers are generally known in the art. Suitable carriers for this invention are those conventionally used large stable macromolecules such as albumin, gelatin, collagen, polysaccharide, monosaccharides, polyvinyl-pyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like. Slow-release carriers, such as hyaluronic acid, may also be suitable. See particularly Prisell et al. (1992) *Int. J. Pharmaceu.* 85:51–56, and U.S. Pat. No. 5,166,331.

The pharmaceutical composition may additionally comprise a solubilizing agent or so-called solubility enhancer. Compounds containing a guanidinium group, most preferably arginine, are suitable solubility enhancers.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* (18$^{th}$ ed.; Mack Pub. Co.: Eaton, Pa., 1990), herein incorporated by reference.

By "treatment" is intended treatment of an existing normal condition that is enhanced by the pharmaceutically active agent, therapeutic treatment of an existing abnormal condition, and preventive or prophylactic procedures performed before the occurrence of an abnormal disorder.

We have recently reported an increase in the expression of fatty acid synthase (FAS), a key enzyme in de novo fatty acid synthesis, in $A^{vy}/a$ mice compared to lean controls. Furthermore, we have also found recombinant agouti protein to stimulate both expression and activity of FAS and to increase triglyceride accumulation in 3T3-L1 adipocytes. Both basal and agonist-stimulated adipocyte lipolysis is impaired in agouti mutant mice compared to their wild-type littermates. This impairment may either be a consequence of the obesity syndrome or it may result from a direct inhibitory effect of agouti on adipocyte lipolysis. However, our recent data demonstrate that it is a direct effect of agouti, as follows. Short-term (1 hr) exposure of human adipocytes to recombinant agouti (100 nM) protein had no effect on basal lipolysis, although longer-term treatment (24 hr) caused a 60% decrease in basal lipolysis (P<0.0001). Short-term agouti treatment totally inhibited ACTH-induced lipolysis (P<0.05). Since melanocortin receptors (MCR) are involved in some actions of agouti, we next determined if agouti's anti-lipolytic effect is exerted through competitive antagonism of the ACTH receptor (MCR-2). 1 $\mu$M forskolin, an adenylate cyclase activator, induced a 48% increase in lipolysis in human adipocytes (P<0.05); this effect was reversed by 100 nM agouti (P<0.005), demonstrating that the anti-lipolytic effect of agouti is distal to the ACTH receptor.

To test the physiological significance of adipose tissue-specific agouti expression in vivo, we generated a mouse line that models the human pattern of agouti in humans. These animals, like humans, express the agouti gene in adipose tissue and do not become obese or diabetic. However, when subjected to daily injections of insulin, they markedly increase their body weight compared with their non-transgenic insulin-treated controls. Similarly, these animals respond to a high sucrose diet with exaggerated weight gain compared to their non-transgenic sucrose-treated controls.

Agouti regulation of pigment development occurs via a paracrine action within the hair follicle, where agouti competitively antagonizes the binding of melanocyte stimulating hormone ($\alpha$-MSH) to its receptor (melanocortin receptor-1, MCR-1). This results in an inhibition of cAMP production and a switch from eumelanin to phaeomelanin production. Agouti has been demonstrated to similarly antagonize other classes of MCRs. Consequently, this competitive antagonism of melanocortin binding has been considered by some investigators to serve as a paradigm for agouti's action in obesity.

However, the actual mechanism of the action of agouti in the development of obesity is not clear. Agouti protein was recently demonstrated to inhibit melanogenesis independent of any melanocortin ligand. Moreover, we have shown that agouti regulates several cellular functions, such as $Ca^{2+}$ signaling, independent of melanocortin receptor antagonism. Furthermore, we have demonstrated that agouti-induced obesity is not antagonized by the melanocortin receptor agonist, NDP-MSH.

Since $[Ca^{2+}]i$ has a key role in the pathogenesis of insulin resistance, obesity and hypertension, we have evaluated the role of the purified agouti gene product in regulating $[Ca^{2+}]i$ in cultured skeletal myocytes, vascular smooth muscle cells, and adipocytes. Agouti cDNA was subcloned into a baculovirus expression vector, packaged, and infected in T. ni cells. The secreted peptide was collected and purified, with media collected from wild-type baculovirus-infected cells serving as controls. Purified agouti induced slow, sustained increases in $[Ca^{2+}]i$ in several cell types, including both murine and human adipocytes. Agouti protein also stimulated lipogenesis in both murine and human adipocytes via an apparently $Ca^{2+}$-dependent mechanism. Since the human homologue of agouti is expressed primarily in adipose tissue, and since $[Ca^{2+}]i$ plays an important role in the metabolic disorders of obesity and insulin resistance, agouti may similarly act via a paracrine mechanism on adipocytes $Ca^{2+}$ signaling and thereby stimulate lipogenesis.

Intracellular $Ca^{2+}$ ($[Ca^{2+}]_i$) plays a key role in the metabolic disorders associated with obesity and insulin resistance (1–3). Obese patients exhibit increased basal $[Ca^{2+}]i$ in adipocytes, while increasing $[Ca^{2+}]i$ in rat adipocytes decreases insulin stimulated glucose transport. Further, $Ca^{2+}$ channel blockade enhances insulin sensitivity in obese and glucose intolerant subjects. Sulfonylureas, such as glibenclamide, are insulin secretagogues widely used to stimulate insulin secretion in the treatment of non-insulin-dependent diabetes mellitus. Sulfonylureas depolarize pancreatic β cells by blocking $K_{ATP}$ channels, thereby resulting in depolarization and secondary $Ca^{2+}$ influx via L-type $Ca^{2+}$ channels, which in turn triggers insulin release (8,9). The β cell receptor for sulfonylureas, sulfonylurea receptor1 (SUR1), has been cloned (10). Recently, Alemzadeh et al reported that the drug diazoxide activates the β cell $K_{ATP}$ channel and subsequently exerts an antiobesity effect in obese Zucker rats (11,12). Further, they recently reported that diazoxide exerted a significant antiobesity effect in hyperinsulinemic obese adults (13). However, this action was attributed to direct actions of diazoxide on β cells, rather than direct effects of diazoxide on adipocyte metabolism. Patients treated with glibenclamide frequently experience weight gain as a side effect. These effects of glibenclamide and diazoxide on body weight have been attributed to their effect on circulating insulin rather than to any direct effect on adipocytes (11–13).

However, SUR agonists have previously been demonstrated to exert direct effects on adipocytes. Draznin et al (2,16) reported that glibenclamide increased $[Ca^{2+}]_i$ in isolated rat adipocytes in a dose dependent manner by promoting $Ca^{2+}$ influx through voltage-dependent $Ca^{2+}$ channels, while this effect was blocked by nitrendipine. Moreover, glibenclamide has been reported to potentiate peripheral insulin effects in isolated adipocytes (24,27). In contrast, Rajan et al (26) were unable to identify high affinity SUR in either isolated rat adipocytes or 3T3-L1 adipocytes. Moreover, they were unable to inhibit $^{86}Rb^+$ efflux (a surrogate for $K_{ATP}$ channel activity) or increase $[Ca^{2+}]_i$ with glibenclamide. The reason for this discrepancy is not clear. However, several other investigators have reported both specific binding of sulfonylurea and specific post-receptor effects in murine and rat adipocytes. For example, rat adipocytes exhibit specific, saturable glibenclamide binding ($K_D$ of 1–3 μM), which is displaced by other sulfonylureas, and sulfonylurea treatment of isolated rat adipocytes potentiates insulin receptor of glucose transport (24,25,27). Further, Muller et al (28,29) reported that glimepiride exhibits specific binding to 3T3-L1 and rat adipocytes, resulting in an insulin-mediated stimulation of glucose transport and non-oxidative glucose disposal. These effects were attributed to sulfonylurea-induced inhibition of cAMP level and protein kinase A activity. Thus, rodent adipocytes may exhibit SUR1 binding and functional response to this binding. However, other data cited above argues that this may not be true. Thus, prior to the present invention there was clearly considerable controversy in this area.

We have demonstrated that the sulfonylurea receptor is expressed and is functional in human adipocytes. Furthermore, we describe the relevance of sulfonylurea-mediated calcium responses and biochemical and physiological actions consistent with a role of this receptor's regulation of energy homeostasis. Finally, we demonstrate that small molecules that regulate adipocyte calcium levels have weight loss effects on rodent obesity models.

Using RT-PCR or any other technique to clone known genes, such as clonal hybridization, cDNA fragments of the SUR1 fragment were identified. Sequence analysis confirmed the identity of this PCR product, which was 100% identical to human SUR1. The selectivity of the SUR1 transcript in adipocytes was shown by the lack of detectable fragment in human preadipocytes and the inability to identify an mRNA transcript by Northern blot analysis. Adipocyte SUR1 expression by Northern blot analysis showed an approximately 5 Kb transcript of SUR1 mRNA in adipose tissue.

The functionality of the SUR1 receptor was determined with respect to calcium mobilization and small molecule effects. $[Ca^{2+}]_i$ response was measured fluorometrically in isolated human adipocytes using a standard method (2,16). Briefly, isolated human adipocytes were incubated in DMEM or any other suitable medium such as Ham's F-10, Modified Eagle's media plus 5–10% fetal calf serum overnight for cell recovery. Prior to $[Ca^{2+}]_i$ measurement, adipocytes were pre-incubated in serum-free medium for 2 hrs, rinsed with HBSS solution containing the following components in mM: NaCl 138, $CaCl_2$ 1.8, $MgSO_4$ 0.8, $NaH_2PO_4$ 0.9, $NaHCO_3$ 4, glucose 20, glutamine 6, HEPES 20 and BSA 1%. Cells were then loaded with fura-2 acetoxymethyl ester (10 μM) in the same buffer for 30–60 min at 37° C. in dark with continuous shaking. To remove extracellular dye, cells were rinsed with HBSS for three times and resuspended in this solution at a concentration of $1-10\times10^5$ cells/ml. $[Ca^{2+}]_i$ was measured using dual excitation (340 and 380 nm) and single emission (510 nm) fluorometry. Following the establishment of stable baseline, the response to a SUR agonist such as glibenclamide (1–20 μM) can be determined. Digitonin (25 μM) and Tris/EGTA (100 mM) were used to measure maximal and minimal fluorescence to calibrate the signals, and final $[Ca^{2+}]_i$ was then calculated by a known method such as described in Grynkiewicz et al (17). Response to glibenclamide showed sustained increases of $[Ca^{2+}]_i$ in human adipocytes in dose-dependent manner. However, human preadipocytes did not exhibit any $[Ca^{2+}]_i$ response to glibenclamide, consistent with the absence of SUR1 in human preadipocytes.

Adipocyte SUR1 also regulated lipogenesis, as demonstrated by human adipocytes treated with SUR1 agonist and antagonist. FAS and GPDH activities are commonly used lipogenic markers, although other markers of lipogenesis will most likely give similar results. Cells treated with a SUR agonist such as glibenclamide caused increased FAS activity between 50%–500% from basal levels, which may be completely blocked by 10 μM diazoxide, a $K_{ATP}$ channel activator or other $K_{ATP}$ channel activators such as pinacidil, cromakalin, nicorandil, aprikalim, and partially inhibited by nitrendipine, an L-type $Ca^{2+}$ channel antagonist or similiar L-type $Ca^{2+}$ channel antagonists characterized by examples from these three classes of compounds: Phenylalkylamines (example, verapamil); Benzothiazepines (example, diltiazem); and dihydropyridines (examples, nitrendipine, nifedipine, amlodipine, felodipine, isradipine, nicardipine, nisoldipine. Similarly, SUR agonists such as glibenclamide stimulated increased GPDH activity between 50–100%, which may be completely blocked by 10 μM diazoxide, a $K_{ATP}$ channel activator, and partially inhibited by nitrendipine, an L-type $Ca^{2+}$ channel antagonist.

Adipocyte SUR1 also regulates lipolysis. Human adipocytes were examined for changes in lipolysis regulation by measurement of glycerol release into the media. Glycerol was measured by using a standard method (19), although other techniques for measuring glycerol would be equally useful. Treatment with SUR agonists such as glibenclamide caused inhibition in lipolysis between 25–70%, which was recovered 75% by 2–10 M diazoxide, a $K_{ATP}$ channel activator, and partially inhibited by 5–50 M nitrendipine, an L-type $Ca^{2+}$ channel antagonist.

Accordingly, using the above techniques and human adipocytes, SUR antagonists that can decrease the lipid accumulation in adipocytes can be identified. Adipocytes were prepared as described in example 3 or as described (patent filed; Jan. 29, 1999; 09/240,029) and cultured as described in these references. Compounds may then be added to the cells and compounds inhibiting glibenclamide-mediated increases may be SUR antagonists, such as nitrendipine. Other methods to determine lipogenesis include determination of total lipid accumulation or the measurement of other lipogenic enzyme activities such as diglyceride acyltransferase. A correlation of calcium mobilization with the biochemical effects observed with sulfonylurea reagents is also clear. Another method to identify SUR antagonists is to use calcium measurements to find SUR antagonists. Using the same methodology described above, one skilled in the art can identify SUR antagonists for human adipocytes.

SUR regulates intracellular calcium after binding of an agonist by inhibiting an inwardly rectifying potassium channel, the $K^+$-ATP channel. Accordingly, various compounds, such as diazoxide, that stimulate these channels will effectively block calcium accumulation. Glibenclamide and diazoxide serve as an antagonistic pair in the pancreatic β-cell, the former increasing intracellular $Ca^{2+}$-stimulated insulin release and the latter inhibiting this process. Incubation of adipocytes with diazoxide prevented increase intracellular calcium in response to sulfonylureas such that there was no detectable response to any dose of glibenclamide in the presence of 2–10 μM diazoxide. This blockade of glibenclamide-induced intracellular calcium signaling also prevented sulfonylurea-induced increases in fatty acid synthase activity and triglyceride. Accordingly, a method to identify such potassium channel activators would involve the use of human adipocytes prepared as described above. The cells are incubated with 1–20 μM glibenclamide as a typical SUR agonist, although others such as glipizide, gliclazide, tobutamide, glimepiride, or chloropamide could be used. The treated cells are then incubated with compounds to determine their ability to inhibit the increase in $[Ca^{2+}]_i$ caused by the SUR agonist as described above. Additionally, measurement of lipogenesis or lipolysis response may also be used as described above.

Calcium channel antagonist treatment has been shown to reverse agouti-induced obesity and insulin resistance in mice. Accordingly, the following method is described to identify calcium channel blockers that can cause weight loss. Common obesity models that can be used in this method include transgenic agouti mice, yellow mice, ob/ob mice, db/db mice, or Zucker rats. Animals are maintained on standard lab chow diets. When significant adiposity is apparent, animals are then treated with the compounds in the appropriate vehicles. Weight loss and food intake was monitored over the course of 1–8 weeks. Fat pad weight can be determined as an endpoint for weight loss. Also, FAS and GPDH activity can be determined in treated and vehicle-treated animals.

The ability to discover novel SUR antagonists and calcium channel blockers would be facilitated by the use of a facile and reproducible assay using human adipocytes as the target cell type. Use of another cell type, such as HEK293 cells, would allow characterization of the adipocyte-selectivity of novel compounds. Accordingly, the following method describes the use of human adipocytes in a screening assay for SUR antagonists and calcium channel blockers.

Human subcutaneous abdominal adipose tissue was obtained from patients undergoing elective abdominal cosmetic surgery, although other types of adipose tissue, such as mesenteric, retroperitoneal, perirenal, or omental may be useful in identifying these compounds. Preadipocytes are isolated by collagenase treatment of the tissue and cultured adipocytes prepared as described (patent filed; Jan. 29, 1999; 09/240,029). Agents that regulate calcium flux in adipocytes as noted above can mediate lipolysis. Human adipocytes may be cultured in multi-well plates with different treatments between 1 hour or 24 hours as indicated, and glycerol release into the culture medium was determined as an indicator for lipolysis using a one-step enzymatic fluorometric method. The media collected from 1 hr treatments were used directly for glycerol measurements. For 24 hr treatments, media were removed, and cells were washed with Hank's Balanced Salt Solution and incubated in fresh medium for a further 10–60 min. This media were then used for glycerol measurements for 24 hr treatments. After medium was collected, cells were processed for total protein concentration by a modified Bradford method using Coomassie Blue dye (PIERCE, Rockford, Ill.) or other comparable protein determination methods to allow correction for differences in cell density/well.

Correlation of lipolysis with flux of intracellular calcium ($[Ca^{2+}]i$) concentration is then performed. Human cultured adipocytes are plated as described above and compounds added for a defined period of time 30–120 minutes. $[Ca^{2+}]i$ levels are then measured fluorometrically using dual excitation (340 and 380 nm)/single emission (510 nm) fluorometry and $[Ca^{2+}]i$ is calculated by the computer in the fluorometer. As a control, after loading fura-2/AM cells are pretreated with nitrendipine (RBI, Natick, Mass.) (30 μM, final concentration) for 10 min at 37° C.

Selectivity of the compounds may then be determined by analysis of intracellular calcium concentrations in a variety of relevant cell types such as 3T3-L1 adipocytes, primary human adipocytes, differentiated cultured adipocytes, smooth muscle cells, pancreatic beta cells, cardiomyocytes and other cell types. Adherent cell types are plated in a multi-well plate and $[Ca^{2+}]i$ levels are then measured fluorometrically using dual excitation (340 and 380 nm)/single emission (510 nm) fluorometry as described above. As a control, after loading fura-2/AM cells are pretreated with nitrendipine (RBI, Natick, Mass.) (30 μM, final concentration) for 10 min at 37° C.

Alternatively, if a novel calcium channel, sulfonylurea receptor, or potassium channel is identified and cloned as described above, a selective assay to screen for molecules that would stimulate a potassium channel or antagonize a sulfonylurea receptor or calcium channel would be developed. In general, such an assay would require the introduction of the cDNA encoding said protein into a cell line commonly used for such purposes such as HEK293. The recipient cell line must be devoid of the introduced protein and that can be determined by analysis of the mRNA of the cell line using the novel cDNA. The expression of this cDNA would be driven by common eukaryotic or viral promoters in order to achieve measurable expression of the cDNA. A drug-resistance gene marker introduced simultaneously with the novel cDNA would facilitate the cloning of the cell line. Many such common examples of the generation of such heterologously expressing cell lines can be found.

The clonal cell line would then be characterized with respect to the level of expression and functionality of the introduced gene product. This would include Northern analysis, calcium channel agonist/antagonists responses, as well as responses to sulfonylureas and $K_{ATP}$ channel agonists.

Methods of the invention are useful for identifying novel sulfonylurea receptor antagonist and/or calcium channel blockers that are selective for adipocytes. Such compounds will be useful in the treatment and control of obesity, diabetes, and other insulin related disorders. Using the methods of the invention, the following information can be obtained: The presence of a novel $K^+$-ATP channel and/or sulfonylurea receptor that will mediate intracellular calcium flux and have therapeutic utility in the treatment of diabetes, obesity or cardiovascular disease; The use of known sulfonylurea receptor and/or calcium channel antagonists that will mediate intracellular calcium flux for therapeutic utility in the treatment of obesity; The use of any adipocyte-specific calcium mobilizing agent for the treatment of obesity; The use of adipocytes (human or murine) to screen for the above described calcium mobilizing agents using similar methodology to that described in the patent; The presence of a novel sulfonylurea receptor and/or calcium channel in the adipocyte that will mediate intracellular calcium flux and have therapeutic utility in the treatment of obesity; The use of the above described channels for the screening and identification of compounds that have therapeutic utility in the treatment of obesity.

EXAMPLES

Example 1

Sulfonylurea receptor is expressed in human adipocytes.

Figure 1A:
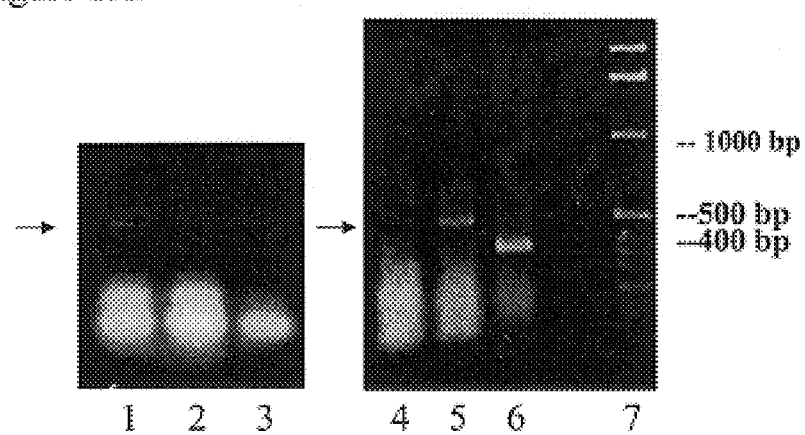
FIG. 1. Detection of the expression of SUR1 gene in human adipocyte by RT-PCR and Northern blot analysis. Total RNA from human preadipocytes and adipocytes and pancreatic β-cells was extracted using $CsCl_2$ density centrifugation. mRNA was isolated according to manufacture's instruction (micro poly(A) pure kit, Ambion Inc, Austin, Tex.). RT-PCR was performed essentially as previously described (7). Briefly, 400 ng of human adipocyte mRNA was reverse-transcribed to first strand cDNA using random-hexamer and reverse transcriptase (Perkin Elmer, Norwalk, Conn.) and amplified by PCR (Perkin Elmer, Norwalk, Conn.). The PCR product, a 490-bp SUR1 fragment (designated by arrow), was visualized by 1.2% agarose gel electrophoresis. The amplified PCR products were then visualized by 1.2% agarose gel electrophoresis, purified (Geneclean kit, Bio 101, Inc) and subjected to sequence analysis using ABI PRISM system (model version 2. 1. 1). Northern blot analysis was conducted as previous described (15). Human adipocyte mRNA (4 μg/well) was run in 1% agarose gel and transferred to nylon membrane, which was hybridized with human SUR1 cDNA probes eluted from PCR products and radiolabeled using a random primer method. Unbound probe was removed by rinsing the membrane with 2× SSC for 30 min at room temperature and 0.1× SSC/0.1% SDS for 45 min at 60° C. Finally, membrane was exposed to X-ray film at -80° C. A. Lane 1: human pancreatic β cells as positive control; lane 2: human preadipocytes without reverse transcriptase; lane 3: human preadipocyte with reverse transcriptase; lane 4: human adipocytes without reverse transcriptase; lane 5: human adipocytes with reverse transcriptase; lane 6: 18 s fragment amplified as RT-PCR system positive control; lane 7: DNA marker. A 5-Kb transcript of SUR1 mRNA was detected in human adipocyte. B. Lane 1: human pancreas mRNA as positive control; lane 2: human adipocyte mRNA; Lane 3: human preadipocyte mRNA.
Figure 1B:
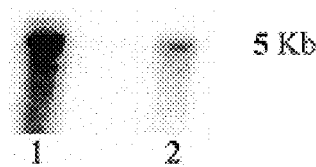

To determine if the sulfonylurea receptor is present in human adipocytes, total RNA from human adipocytes was extracted using $CsCl_2$ density centrifugation. mRNA from human adipocyte was isolated according to manufacture's instruction (micro poly(A) pure kit, Ambion Inc, Austin, Tex.). RT-PCR was performed essentially as previously described (7). Briefly, 400 ng of human adipocyte mRNA was reverse-transcribed to first strand cDNA using random-hexamer and reverse transcriptase (Perkin Elmer, Norwalk, Conn.) and amplified by PCR (Perkin Elmer, Norwalk, Conn.). The PCR conditions were as follows: initial denaturation at 94° C. for 5 min, followed by 34 cycles of denaturation at 94° C. for 45 s, annealing at 55° C. for 1 min, and extension at 72° C. for 2 min, with a final extension step at 72° C. for 8 min with 0.5 μM 5' primer (not shown) and 3' primer (not shown) which correspond to nucleotide positions 4206–4230 and 4664–4689 in HSU63421 respectively. The amplified PCR products were then visualized by 1.2% agarose gel electrophoresis, purified (Geneclean kit, Bio 101, Inc) and subjected to sequence analysis using ABI PRISM system (model version 2. 1. 1). Northern blot analysis was conducted as previous described (15). Human adipocyte mRNA (4 μg/well) was run in 1% agarose gel and transferred to nylon membrane, which was hybridized with human SUR1 cDNA probes eluted from PCR products and radiolabeled using a random primer method. Unbound probe was removed by rinsing the membrane with 2× SSC for 30 min at room temperature and 0.1× SSC/0.1% SDS for 45 min at 60° C. Finally, membrane was exposed to X-ray film at −80° C. As shown in FIG. 1, the sulfonylurea receptor mRNA was the only observed in adipocytes.

Example 2

The adipocyte sulfonylurea receptor regulates lipolysis and lipogenesis.

To study the role of adipocyte SUR1 in regulating lipogenesis, we treated human adipocyte with SUR1 agonist and antagonist using FAS and GPDH activities as lipogenic markers. Human adipocytes were incubated in 24-well plates with the treatments indicated for 48 hr. FAS and GPDH activities were determined spectrophotometrically in crude cytosolic extracts of human adipocytes by measuring the oxidation rate of NADPH or NADH respectively, as previously described (14). The protein correction was measured by a modified Bradford method using Coomassie Blue dye (Pierce, Rockford, Ill.). 10 μM glibenclamide caused a 67% increase in adipocyte FAS activity (0.692±0.052 NADPH nM/min/mg protein vs. 1.154±0.010 NADPH nM/min/mg protein, p<0.001, FIG. 3A), which was completely blocked by 10 μM diazoxide, a $K_{ATP}$ channel activator, and partially inhibited by nitrendipine, an L-type $Ca^{2+}$ channel antagonist. Similarly, 10 μM glibenclamide stimulated a 48% increase in GPDH activity (554.0±33.0 NADH nM/min/mg protein vs. 821.0±73.4 NADH nM/min/mg protein, p<0.01, FIG. 3B), which was totally blocked by 10 μM diazoxide.

We next investigated the role of adipocyte SUR1 on lipolysis. Lipolysis was measured as follows. Human adipocytes were treated as described below and glycerol release into the culture medium was determined as an indicator for lipolysis using a one step enzymatic fluorometric method (19). After treatment medium was obtained, $HClO_4$ was added for deproteinization. The sample was next centrifuged to precipitate protein and the supernatant was neutralized with NaOH before glycerol assay. 48 hr-treatment with 10 μM glibenclamide caused a 68% inhibition in lipolysis (0.193±0.050 NADH μM/mg protein vs. 0.061±0.009 NADH μM/mg protein, p<0.05, FIG. 4), which was recovered to 75% and 50% by diazoxide and nitrendipine, respectively

Example 3

Compounds that modulate SUR activity in adipocytes mediates biochemical parameters that influence obesity and diabetes.

Human subcutaneous abdominal adipocytes were isolated from healthy patients undergoing cosmetic liposuction using methodology we have previously described. Briefly, the tissue was washed several times with Hank's Balanced Salt Solution, minced into small fragments and digested with type I collagenase (1 mg/mL) in a shaking water bath at 37° C. for 30–40 minutes. Cells were then filtered through a sterile nylon filter (500 μm mesh) and cultured in Dulbecco's Modified Eagle's Medium (DMEM) supplemented with 1% fetal bovine serum, 1% bovine serum albumin, 100 U/mL penicillin, 100 μg/mL streptomycin and 50 μg/mL gentamicin. Cells were subsequently cultured in suspension in sterile polypropylene flasks in a humidified 37° C./5% $CO_2$ incubator. After one day, suspended (floating) adipocytes were transferred to fresh medium and maintained as a thin layer at the top of the culture medium to ensure access to nutrients. The cells were maintained for another 24 hours in this medium and then changed to fresh medium with the addition of SUR agonists (such as glibenclamide) for up to 48 hours with the compounds to be tested. Medium was changed every 24 hours, and cell viability was verified with trypan blue exclusion at the end of representative experiments.

Exposure of human adipocytes to graded doses of the sulfonylurea, glibenclamide, resulted in slow, sustained increases in intracellular free calcium levels. The maximum response is 388±72 nM over a baseline of 190 nM for human adipocytes. For human adipocytes, the $EC_{50}$ is approximately 1 µM. This sulfonylurea-mediated increase in adipocyte intracellular calcium is linked to increases in human adipocyte fatty acid synthase activity. Glibenclamide (2 µM) increased fatty acid synthase activity from 1.93±0.24 to 7.90±0.4 nmol/min/mg protein. A further increase, to 12.8±0.6 nmol/min/mg was noted with 10 µM glibenclamide (p<0.001). This resulted in a dose-responsive stimulation of triglyceride accumulation, from 28.2±4.5 to 46.1±6.3 to 58.0±3.4 µg/mg protein.

To prove a correlation of calcium mobilization with the biochemical effects observed with sulfonylurea reagents, the effect of calcium channel antagonists on the sulfonylurea mediated triglyceride accumulation was examined. First, the dihydropyridine calcium channel antagonist, nitrendipine, completely blocked the sulfonylurea mediated increases in adipocyte intracellular calcium levels. This block of intracellular calcium results in inhibition of increased fatty acid synthase activity and triglyceride accumulation in response to sulfonylureas. The aforementioned increase in increased fatty acid synthase activity from 1.93±0.24 to 7.90±0.4 nmol/min/mg protein in response to 2 µM glibenclamide was decreased to 2.12±0.0.43 nmol/min/mg protein, which was not significantly different from control, when 30 µM nitrendipine was included.

Example 4

Compounds that modulate intracellular calcium concentration in adipocytes mediate biochemical parameters that influence obesity and diabetes.

Adipocytes exposed to KCl (40 mM, to depolarize and activate voltage gated $Ca^{2+}$ channels) for two hours and then harvested approximately 72 hours later exhibited a two-fold increase in fatty acid synthase activity, from 3.93±0.11 to 6.24±0.2 nmol NADPH/min/mg protein (p<0.01). Similarly, stimulation of receptor-mediated $Ca^{2+}$ influx with either parathyroid hormone (PTH; 4.8 nM) or arginine vasopressin (AVP; 1 nM) also resulted in a two-fold increase in fatty acid synthase activity, to 6.9±0.1 nmol/min/mg protein (p<0.01). Exposure to these $Ca^{2+}$ agonists also inhibited lipolysis. Twenty-four hour exposure to mild depolarization with KCl (10 mM) resulted in a decrease in lipolysis to 75.9±4.1% of control levels (p<0.005). Short-term (one-hour) experiments with more complete depolarization demonstrate that depolarizing human adipocytes with 25 and 40 mM KCl inhibited forskolin-induced lipolysis by 42±5 and 50±1.7%, respectively (p<0.05). Similarly, short-term treatment with 1 nM AVP caused a 56±6.6% inhibition of forskolin-induced lipolysis (p<0.01).

Stimulation of fatty acid synthase and concomitant inhibition of lipolysis results in increased lipid accumulation in human adipocytes. Adipocytes were treated as described above, harvested, and their triglyceride content was analyzed and normalized for protein content. Treatment with KCl (40 mM) or PTH (4.8 nM) resulted in significant increases in triglyceride content, from 30.3±0.3 (control) to 43.5±0.5 (KCl) and 54.5±0.6 (PTH) µg/mg protein (p<0.01). Similarly, a two-hour exposure to 10 nM of the $Ca^{2+}$ ionophore, A23187, resulted in a marked increase in triglyceride accumulation over the ensuing 48 hours, from 31.4±2.4 to 52±7 µg/mg protein (p<0.001). Thus, these calcium-stimulated biochemical activities will contribute to the development of adipocyte hypertrophy and potentially obesity.

Calcium channel antagonists do the opposite of that described above. Use of non-selective calcium channel antagonists will inhibit fatty acid synthase activity, stimulate lipolysis and decrease triglyceride accumulation in calcium-stimulated human adipocytes. For example, 30 µM nitrendipine resulted in complete inhibition of each of the calcium-stimulated activities noted above. Moreover, the well-known activation of lipogenesis by insulin (1 nM) was completely inhibited by nitrendipine. Insulin increased fatty acid synthase activity from 3.95±0.11 to 14.56±0.22 nmol/min/mg protein (p<0.0001), while inclusion of nitrendipine (30 µM) completely prevented this increase (4.12±0.03 nmol/min/mg). Similarly, inclusion of nitrendipine caused a 40% reduction in insulin-stimulated triglyceride accumulation (p<0.001).

Glibenclamide regulates intracellular calcium by inhibiting an inwardly rectifying potassium channel, the $K^+$-ATP channel. This results in depolarization and consequent activation of voltage-gated $Ca^{2+}$ channels. Accordingly, various compounds, such as diazoxide, that stimulate these channels will effectively block calcium accumulation. Glibenclamide and diazoxide serve as an antagonistic pair in the pancreatic β-cell, the former increasing intracellular $Ca^{2+}$-stimulated insulin release and the latter inhibiting this process. Since we found glibenclamide to stimulate adipocyte intracellular $Ca^{2+}$ despite there having been no previous report of adipocytes expressing any type of sulfonylurea receptor, we examined whether diazoxide would antagonize this effect. Incubation of adipocytes with diazoxide prevented increase intracellular calcium in response to sulfonylureas such that there was no detectable response to any dose of glibenclamide in the presence of 5 µM diazoxide. Accordingly, this blockade of glibenclamide-induced intracellular calcium signaling also prevented sulfonylurea-induced increases in fatty acid synthase activity and triglyceride. The aforementioned increases in fatty acid synthase activity, from 1.93±0.24 (control) to 7.90±0.4 (2 µM glibenclamide) to 12.8±0.6 (10 µM glibenclamide) nmol/min/mg protein was completely prevented by inclusion of 5 µM diazoxide. Fatty acid synthase activity in the presence of diazoxide and 2 or 10 µM glibenclamide was 1.00±0.10 and 1.21±0.31, respectively; these values were not significantly different from control (1.93±0.26). Further, as an apparent consequence of hyperpolarizing the adipocytes, diazoxide (5 µM) also inhibited the lipogenic response to 40 mM KCl, as reflected in an inhibition of KCl-activated fatty acid synthase activity. Fatty acid synthase activity was increased from 2.87 (control) to 6.20±0.57 nmol/min/mg protein in response to 40 mM KCl (p<0.01). This response was decreased to 3.24±0.41 nmol/min/mg protein (not significantly different from control) in the presence of 5 µM diazoxide. Similarly, fatty acid synthase activity in the presence of 1 nM insulin was 14.56±0.22 nmol/min/mg protein and was reduced 7.08±0.10 nmol/min/mg in the presence of 1 nM insulin and 5 µM diazoxide.

Example 5

Isolation and identification of a novel calcium regulatory channel/receptor from human adipose tissue/adipocytes.

See Example 1 for a specific example of this technique. mRNA from human adipose tissue or human preadipocytes and adipocytes induced to differentiate is isolated. To determine if novel calcium channels or other calcium regulatory channels and receptors such as the potassium ATP channel or sulfonylurea receptors are present, the following methods have been performed.

A polymerase chain reaction (PCR) technique using primers that have been optimized for the synthesis of a region of the $α_1$-subunit of the calcium channel was performed. The primers used flank a low degeneracy region of the $\alpha_1$-subunit that is well conserved between cardiac and skeletal muscle and is conserved across species (human, hamster, rabbit, mouse). RNA was isolated from subcutaneous adipocytes from four different patients and in visceral adipocytes from one patient, and first strand cDNA synthesis was conducted using a standard reverse transcriptase method, followed by PCR as using the primers indicated. The PCR products were separated and visualized by electrophoresis through a 0.7% agarose gel containing 1% ethidium bromide. In each case, two bands were noted. Both are within the expected size range (950–1,000 base pairs).

Alternatively, traditional methods such as low stringency hybridization using the cDNA probes of the various human channels or PCR using degenerate oligonucleotides can be performed on the cDNA libraries available from the human preadipocyte and adipocytes.

Example 6
Method for screening compounds that affect calcium levels in human adipocytes Human subcutaneous abdominal adipose tissue was obtained from patients undergoing elective abdominal cosmetic surgery. These patients were normal, with no known history of metabolic disorders. Isolated adipocytes were prepared from human adipose tissue by methods available in the art. Briefly, adipose tissue was washed with Hanks solution, roughly chopped with scissors and digested in Hanks solution containing collagenase type 1 (1 mg/ml) for 1 hr at 37° C. Collagenase was washed out with HEPES buffered salt solution (HBSS) containing 138 mM NaCl, 1.8 mM $CaCl_2$, 0.8 mM $MgSO_4$, 0.9 mM $NaH_2PO_4$, 4 mM $NaHCO_3$, 25 mM glucose, 6 mM glutamine, 20 mM HEPES, 0.5% bovine serum albumin at the end of digestion. Cells were then filtered through a sterile nylon filter (500 $\mu$m mesh), and cultured in Dulbecco's Modified Eagle's Medium (DMEM) supplemented with 1% fetal bovine serum (FBS), 1% bovine serum albumin (BSA), 100 U/ml penicillin, 100 $\mu$g/ml streptomycin and 50 $\mu$g/ml gentamicin.

Agents that regulate calcium flux in adipocytes as noted above can mediate lipolysis. Human adipocytes (1 mL cells/well) were incubated in 24-well plates with different treatments for either 1 hour or 24 hours as indicated, and glycerol release into the culture medium was determined as an indicator for lipolysis using a one-step enzymatic fluorometric method. The media collected from 1 hr treatments were used directly for glycerol measurements. For 24 hr treatments, media were removed, and cells were washed with Hank's Balanced Salt Solution and incubated in fresh medium for a further 30 min. This media were then used for glycerol measurements for 24 hr treatments. After medium was collected, $HClO_4$ was added to give a final concentration of 3% for deproteinization. The sample was centrifuged at 9000x g for 20 min. The supernatant was then collected and neutralized with 10 N NaOH. Samples were stored at −80° C. prior to glycerol assay. Cells were collected, homogenized and stored at −80° C. for subsequent total protein correction by a modified Bradford method using Coomassie Blue dye (PIERCE, Rockford, Ill.).

Correlation of lipolysis with flux of intracellular calcium ($[Ca^{2+}]i$) concentration is then performed. $[Ca^{2+}]i$ is measured in primary adipocytes. For primary adipocytes, 3 ml of cells are resuspended in 6 ml of HBSS and fura-2/AM was loaded for 80 min at 37° C. Extracellular fura-2/AM is washed three times with HBSS by centrifugation. $[Ca^{2+}]i$ levels are then measured fluorometrically in suspensions using dual excitation (340 and 380 nm)/single emission (510 nm) fluorometry and $[Ca^{2+}]i$ is calculated by the computer in the fluorometer. As a control, after loading fura-2/AM cells are pretreated with nitrendipine (RBI, Natick, Mass.) (30 $\mu$M, final concentration) for 10 min at 37° C.

Selectivity of the compounds may then be determined by analysis of intracellular calcium concentrations in a variety of relevant cell types. $[Ca^{2+}]i$ was measured in L6, A7r5 and HEK-293 cells in 3T3-L1 cells. Monolayers of non-fused L6 cells and confluent A7r5 cells after 14–16 hrs starvation in a serum free culture media were rinsed with Hanks solution and detached by incubation in 2 ml of trypsin (0.05%) for 2–3 min at 37° C. and released by pipetting with culture media containing serum. Confluent HEK-293 cells after 3–4 hrs starvation in a serum free culture media were released just by pipetting without trypsinization. Cells were harvested by centrifugation at 50x g, and resuspended in 1 ml of HBSS at a density of approximately $10^6$ cells/ml. For 3T3-L1 cells, monolayers of differentiated adipocytes were rinsed with serum-free DMEM and exposed to 0.05% trypsin for 3 min. The solution was decanted, and the cells were incubated for 3 min in culture media. Cells were detached by pipetting and collected by centrifugation at 50x g. Cells were then incubated in culture media to recover for 1 hr followed by incubation in serum free DMEM for 4 hrs at 37° C. in an atmosphere of 5% $CO_2$, and collected by centrifugation and resuspended in HBSS at a density of approximately 106 cells/ml. Cell suspensions were chilled in ice for 5 min and loaded with 10 mM fura-2/AM (final concentration) (Sigma, St Louis, Mo.) in the dark for 20 min at 37° C. For 3T3-L1 adipocytes chilling step was skipped. For the $[Ca^{2+}]i$ measurements L6, A7r5, HEK-293 cells and 3T3-L1 cells were resuspended in 1 ml of HBSS and transferred to a 1-ml, 37° C. cuvette and primary adipocytes were resuspended in 3–5 ml of HBSS at the concentration of ~20x$10^4$ cells/ml and 2.4 ml of cell suspension were transferred to a 3-ml, 37° C. cuvette. $[Ca^{2+}]i$ levels were then measured fluorometrically in suspensions using dual excitation (340 and 380 nm)/single emission (510 nm) fluorometry and $[Ca^{2+}]i$ was then calculated by the computer in the fluorometer.

Alternatively, if a novel calcium channel, sulfonylurea receptor, or potassium channel is identified and cloned as described above, a selective assay to screen for molecules that would stimulate a potassium channel or antagonize a sulfonylurea receptor or calcium channel would be developed. In general, such an assay would require the introduction of the cDNA encoding said protein into a cell line commonly used for such purposes such as HEK293. The recipient cell line must be devoid of the introduced protein and that can be determined by analysis of the mRNA of the cell line using the novel cDNA.

The expression of this cDNA would be driven by common eukaryotic or viral promoters in order to achieve measurable expression of the cDNA. The cloning of the cell line would be facilitated by a drug-resistance gene marker introduced simultaneously with the novel cDNA. Many such common examples of the generation of such heterologously expressing cell lines can be found.

The clonal cell line would then be characterized with respect to the level of expression and functionality of the introduced gene product. This would include Northern analysis, calcium channel agonist/antagonists Reponses, as well as responses to sulfonylureas and KATP channel agonists.

A screen to identify molecules that mediates intracellular calcium via this gene product may then be established using essentially the same techniques as described above for the HEK293 cell type. A multiwell plate format to observe changes of intracellular calcium may be established. One example of such a format is found in FIG. 5. Using human adipocytes, we are able to measure intracellular calcium changes in response to KCl.

Example 7

Determination of adipocyte selective calcium antagonist compounds utility in treating obesity/diabetes Use of a transgenic model of obesity and insulin resistance is described. It should be noted that most genetic and diet-induced models of obesity/diabetes would be suitable for this purpose.

Transgenic mice were generated by methods in the art. In short, transgenic mice were made by pronuclear microinjection of a β-actin promoter-agouti transgene into FVB/N single cell embryos and maintained on the FVB/N background. The following demonstrates that this is a suitable model for this purpose.

Prior to being placed on the experimental diets, 7-week-old male transgenic and control mice were acclimatized on a powdered high-fat diet (Mouse Diet 5015, PMI Feeds, ≧11% fat) for 1 week. They were randomly assigned to either a control or nifedipine (Sigma, St. Louis, Mo.) (1 g/kg diet) diet and were fed ad libitum for 30 days. Food intakes were measured every other day. On day 27, food was held overnight for 12 hr fasting and blood was collected from the tail vein for glucose determination, followed by refeeding. On day 30, animals were anesthetized with sodium pentobarbital (50 mg/kg body weight) (Abbott Lab. North Chicago, Ill.) and blood was obtained by cardiac puncture for blood glucose and plasma triglyceride and insulin determination. Fat pads (epididymal, perirenal, retroperitonaeal, inguinal, and subscapular fats) were dissected, immediately weighed, frozen in liquid nitrogen, and stored at −80° C. FAS activity was measured in adipose tissues as described below. Blood glucose was measured using blood glucose monitoring system (Milpitas, Calif.). Plasma triglyceride levels were measured spectrophotometrically using an enzyme-based assay kit (Sigma, St. Louis, Mo.), and plasma insulin levels were measured by radioimmunoassay kit (INCSTAR, Stillwater, Minn.). Fatty acid synthase activity was measured by a modification of the spectrophotometric method. Subcutaneous adipose tissue were sonicated (1:3 wt/vol) in 250 mM sucrose buffer containing 1 mM EDTA (Gibco, Gaithersburg, Md.), 1 mM dithiothreitol and 100 $\mu$M phenylmethylsulfonyl fluoride (Sigma, St. Louis, Mo.) (pH 7.4). Homogenates were centrifuged at 14,000-x g for 15 min (at 4° C.), and the supernatants were used for enzyme assays. Assays were started by the addition of malonyl CoA, and enzyme activities were expressed as nmol NADPH oxidized/min/mg of protein. Protein was determined by the modified method of Lowry using bovine serum albumin as a standard. All data were presented as mean ±SE for four groups of mice; control mice on control diet, control mice on nifedipine diet, transgenic mice on control diet, and transgenic mice on nifedipine diet. Data were analyzed via two-way (diet×animal) analysis of variance or, in cases where only two groups were being compared, by Student's t-test.

At study initiation (8 weeks of age), transgenic mice ubiquitously expressing agouti (n=12) exhibited significantly higher body weight than the control mice (n=10) (30.54±0.66 vs. 27.26±0.28 g; p<0.001). The increased body weight of the transgenic mice was maintained over the 30 days on diet, and nifedipine was without effect in both groups. The transgenic mice also exhibited an approximately 2-fold increase in fat pad mass (both visceral and subcutaneous) compared to the control mice (2.62±0.27 vs. 1.21±0.19 g; p=0.002). However, nifedipine treatment resulted in a significant reduction in fat pad weight, compared to control diet (1.81±0.14 vs. 1.58±0.23 g, p<0.001 in visceral [epidydimal, perirenal and retroperitoneal] fat; 0.81±0.14 vs. 0.62±0.1, p=0.02 in subcutaneous [inguinal and subscapular]fat) in the transgenic mice, but was without effect in the control mice. The total weight of the five fat pads measured was decreased by 18% in the nifedipine-treated transgenic animals (p<0.007). Gastrocnemius muscle weight was not different between control and transgenic mice however, nifedipine treatment significantly increased gastrocnemius muscle weight by 12% compared to the control diet (0.284±0.005 vs. 0.253±0.005 g; p=0.0009) in the transgenic mice, and was without effect in the control mice. This combination of reduced fat pad mass and increased muscle mass may explain the lack of nifedipine effect on body weight in the transgenic mice. To test the role of de novo fatty acid synthesis in agouti-associated obesity, we measured the activity of FAS in adipose tissue. The transgenic mice exhibited a 7.2-fold increase in FAS activity in subcutaneous adipose tissue compared to the control mice, while nifedipine treatment completely prevented this stimulation of FAS. The transgenic mice had approximately 2-fold higher fed plasma insulin levels than the control mice (p<0.05) (Table 1). Nifedipine treatment completely blocked the hyperinsulinemia in the transgenic mice, but was without effect on the control mice (Table 1). Nifedipine treatment also improved insulin sensitivity, as manifested by the fall in plasma insulin to glucose ratio in the transgenic mice (p<0.05) (Table 1). Nifedipine treatment was without effect on blood glucose levels in either fasted or fed mice. There was also no effect of nifedipine on fasted plasma triglyceride contents (Table 1).

TABLE 1

Blood Glucose and Plasma Insulin and Triglyceride Levels

| Animal | Control | | Transgenic | |
|---|---|---|---|---|
| Treatment | Control | Nifedipine | Control | Nifedipine |
| Glucose (mg/dl) | | | | |
| (fasted) | 121.3 ± 6.5 | 125.3 ± 7.8 | 115.5 ± 8.9 | 100.4 ± 15.2 |
| (fed) | 243.0 ± 7.6 | 213.8 ± 18.6 | 230.6 ± 21.6 | 235.8 ± 9.7 |
| Insulin (ng/ml) (fed) | 14.96 ± 5.3 | 16.74 ± 8.69 | 32.39 ± 4.9* | 13.40 ± 1.96 |
| Insulin/ Glucose (fed) | 0.06 ± 0.02 | 0.084 ± 0.05 | 0.140 ± 0.02* | 0.057 ± 0.01 |
| Triglyceride (mg/dl) (fasted) | 107 ± 14.2 | 83.4 ± 20.1 | 76.5 ± 11.6 | 62.8 ± 5.6 |

Values are the mean ± SE. Data were compared in a row.
p < 0.05

The following references are herein incorporated by reference:

Michaud et al., J Endocrinol. November 1997; 155(2): 207–209; Kim et al., Am J Physiol. March 1997; 272(3 Pt 1): E379–E384; Mynatt et al., Proc Natl Acad Sci USA. Feb. 4, 1997; 94(3): 919–922; Kim et al., FASEB J. December 1996; 10(14): 1646–1652; Maher et al., J Nutr. October 1996; 126(10): 2487–2493; Raynor et al., J Am Diet Assoc. September 1996; 96(9): 854; Jones et al., Am J Physiol. July 1996; 271(1 Pt 1): E44–E49; Jones et al., Am J Physiol, January 1996; 270(1 Pt 1): E192–E196; Maher et al., J Nutr. October 1995; 125(10): 2618–2622; Kaplan et al., J Pediatr. August 1995; 127(2): 200–205; Zemel MB, J Nutr. June 1995; 125(6 Suppl): 1715S–1743S; Zemel MB, J Nutr. June 1995; 125(6 Suppl): 1715S–1717S; Zemel MB et al., Proc Natl Acad Sci USA. May 23, 1995; 92(11): 4733–4737; Kim et al., J Nutr. May 1994; 124(5): 713–716; Abel et al., Am J Hypertens. June 1993; 6(6 Pt 1): 500–504; Zemel et al., Am J Physiol. March 1992; 262(3 Pt 1): E368–E371; Ambrozy et al., Am J Hypertens. July 1991; 4(7 Pt 1): 592–596; Sowers et al., Am J Hypertens. July 1991; 4(7 Pt 2): 466S–472S; Zemel et al., Am J Hypertens. June 1991; 4(6): 537–539.

1. Byyny, R. L., Loverde, M., Llotd, S., Mitchell, W., and Draznin, B. (1992) Cytosolic Calcium and insulin resistance in elderly patients with essential hypertension. Am.J. Hypertension.5, 459–464

2. Draznin, B., Sussman, K. E., Eckel, R. H., Kao, M., Yost, T. and Sherman, N. A. (1988) Possible role of cytosolic free calcium concentrations in mediating insulin resistance of obesity and hyperinsulinemia. J. Clin Invest 82, 1848–1852

3. Draznin, B., Sussman, K., Kao, K., Lewis, D. and Sherman, N. (1987) The existence of an optimal range of cytosolic free calcium for insulin-stimulated glucose transport in rat adipocytes. J.Biol.Chem. 262, 14385–14388

4. Kim, J. H., Kiefer, L. L., Woychik, R. P., Wilkison, W. O., Truesdale, A., Ittoop, O., Willard, D., Nichols, J. and Zemel, M. B. (1997) Agouti regulation of intracellular calcium. Role of melanocortin receptor. Am.J. Physiology. 272, E379–E384

5. Zemel, M. B., Kim, J. H., Woychik, R. P., Michaud, E. J., Kadwell, S. H., Patel, I. R. and Wilkison, W. O. (1995) Agouti regulation of intracellular calcium: role in the insulin resistance of viable yellow mice. Proc.Natl.Acad.Sci.USA. 92, 4733–4737

6. Jones, B. H., Kim, J. H., Zemel, M. B., Woychik, R. P., Michaud, E. J., Wilkison, W. O. and Moustaid, N. (1996) Upregulation of adipocyte metabolism by agouti protein: possible paracrine actions in yellow mouse obesity. Am.J. Physiol. 270, E192–E196

7. Xue, B. Z, Moustaid, N., Wilkison, W. O and Zemel, M. B. (1998) The agouti gene product inhibits lipolysis in human adipocytes via a $Ca^{2+}$-dependent mechanism. FASEB J. Vol. 12, 1391–1396

8. Ashcroft, S. J. H and Ashcroft, F. M. (1990) Cell.signaling 2, 197

9. Sturgess, N. C., Ashford, M. L. J., Cook, D. L., Hales, C. N. (1985) The sulfonylurea receptor may be an ATP-sensitive potassium channel. Lancet 2, 474

10. Bryan, L. A., Nichols, C. G., Wechsler, S. W., Clement, J. P., Boyd, A. E., Gonzalez, G., Sosa, H. H., Nguy, K., Bryan, J.,Nelson, D. A. (1995) Cloning of the β cell high-affinity sulfonylurea receptor: a regulator of insulin secretion. Science. 268, 423–426

11. Alemzadeh, R, Slonlm, A. E., Zdanowicz, M. M and Maturo, J. (1993) Modification of insulin resistance by diazoxide in obese Zucker rats. Endocrinology 133, 705–712

12. Alemzadeh, R., Jacobs, A. W and Pitukcheewnont, P. (1996) Antiobesity effect of diazoxide in obese Zucker rats. Metabolism. 45, 334–341

13. Alemzadeh, R., Langley, G., Upchurch, L., Smith, P., Slonim, A. E. (1998) Beneficial effect of diazoxide in obese hyperinsulinemic adults. J. Clin. Endocr. Met. 83, 1911–1915

14. Moustaid, N., Jones, B. H and Taylor, J. W. (1996) Insulin increases lipogenic enzyme activity in cultured human adipocytes. J. Nutr. 126, 865–870

15. Jones, B. H., Standridge, M. K and Moustaid, N. (1997) Angiotensin II increases lipogenesis in 3T3-L1 and human adipose cells. Endocrinology 138, 1512–1517

16. Draznin, B., Kao, M. and Sussman, K. E. (1987) Insulin and glyburide increase cytosolic free-$Ca^{2+}$ concentration in isolated rat adipocytes. Diabetes, 36:174–177

17. Grynkiewicz, G., Poenie, M. and Tsien, R. Y. (1985) A new generation of $Ca^{2+}$ indicators with greatly improved fluorescent properties. J. Biol. Chem. 260, 3440–3450

18. Kwon, H. Y., Bultman, S. J., Loffeler, C., Chen, W., Furdon, P. J., Powell, J. G., A. L. Usala, Wilkison, W. O., Hansmann, I., Woychik, R. P. (1994) Molecular structure and mapping of the human homolog of the agouti gene. Proc Natl Acad Sci USA 91, 9760–9764

19. Boobis, L. H., and Manghan, R. J. (1983) A simple one-step enzymatic fluorometric method for the determination of glycerol in 20 ul of plasma. Clin. Chim. Acta. 132, 173–179

20. Bokvist, K., Ammala, C., ashcroft, F. M., Berggren, P. O., Larsson, O., Rorsman, P. (1991) Separate process mediate nucleotide-induced inhibition and stimulation of the ATP-regulated $K^+$-channels in mouse pancreatic β-cells. Proc. R. Soc. London ser. B 243, 139–144

21. Gilon, P., Shepherd, R. M., Henquin, J. C. (1993) Oscillations of secretion driven by oscilltions of cytoplasmic $Ca^{2+}$ as evidenced in single pancreatic islets. J. Biol. Chem. 268, 22265–22268

22. Philipson. Louis. H. (1995) ATP-sensitive $K^+$ channels: paradigm lost, paradigm regained. Science. 270, 1159

23. Thomas. P. M., Cote, G. J., Wohllk, N., Haddad, B., Mathew, P. M., Rabl, W., Bryan, L. A., Gagel, R. F., Bryan, J. (1995) Mutations in the sulfonylurea receptor gene in familial persistent hyperinsulinemic hypoglycemia of infancy. Science. 268, 426–429

24. Jacobs, D. B., Jung, C. Y. (1985) Sulfonylurea potentiates insulin-induced recruitment of glucose transport carrier in rat adipocytes. J. Bio. Chem. 260, 2593–2596

25. Maloff, B. L., Lockwood, D. H. (1981) In vitro effects of a sulfonylurea on insulin action in adipocytes. J. Clin. Invest. 68, 85–90

26. Rajan, A. S., Zhao, L. T., Barbara, K. B., John, P. C., Samuel, W. C., Aubrey, E. B. (1994) Do adipocytes contain high affinity sulfonylurea receptor? Endocrinology. 134, 1581–1588

27. Martz, A., Jo, I., Jung, C. Y. (1998) Sulfonylurea binding to adipocyte membrane and potentiation of insulin stimulated hexose transport. J. Biol. Chem. 264, 13672–13678

28. Muller, G., Geisen, K. (1996) Characterization of the molecular mode of action of the sulfonylurea, glimepiride at adipocytes. Horm. Metab. Res. 28: 469–487

29. Muller, G., Wied, S., Wetekam, E- M., Crecelius, A., Unkelbach, A., Punter, J. (1994) Stimulation of glucose utilization in 3T3-L1 adipocytes and rat diaphragm in vitro by the sulfonylureas, glimepiride and glibenclamide, is correlated with modulations of the cAMP regulatory cascade. Biochem. Pharmacol. 48, 985–996

30. Inagaki, N., Gonoi, T., Clement, J. P., Namba, N., Inazawa, J., Gonzalez, G., Bryan, L. A., Seino, S., Bryan, J. (1996) Reconstitution of $I_{KATP}$: an inward rectifier subunit plus the sulfonylurea receptor. Science. 270, 1167–1170

31. Chagnon, Y. C., Perusse, L., Boochard, C. (1998) The human obesity gene map: the 1997 update. Obesity. Res. 6, 76–92

32. Hani, E. H., Clement, K., Velho, G., Vionnet, N., Hager, J., Philippi, A., Dida, L., Inove, H., Permott, M. A., Basdevant, A., North, M., Demenais, F., Guy-Grand, M., Frogvel, P. (1997) Genetic studies of the sulfonylurea receptor gene locus in NIDDM and in morbid obesity among French Caucasians. Diabetes. 46, 688–694

That which is claimed:

1. A method of determining the ability of a compound to act as a SUR1 potassium channel activator, comprising:
   (a) incubating cultured human adipocytes in the presence and absence of said compound, and
   (b) comparing the level of at least one lipogenic or anti-lipolytic marker in said adipocytes after incubation in the presence and absence of said compound, wherein a difference in the level of said marker is correlated to the ability of the compound to act as a SUR1 potassium channel activator.

2. The method of claim 1, wherein said cultured adipocytes are incubated with a SUR1 agonist in the presence and absence of said compound.

3. The method of claim 1, wherein the lipogenic marker is selected from the group consisting of $Ca^{2+}$ influx, FAS activity, GPDH activity and triglyceride accumulation.

4. The method of claim 1, wherein said anti-lipolytic marker is glycerol release into the culture medium or increased intracellular cAMP levels.

5. A method of determining the ability of a compound to act as an adipocyte potassium channel activator, comprising:
   (a) incubating cultured human adipocytes in the presence and absence of said compound, and
   (b) comparing the level of at least one lipogenic or anti-lipolytic marker in said adipocytes after incubation in the presence and absence of said compound, wherein a difference in the level of said marker is correlated to the ability of the compound to act as an adipocyte potassium channel activator.

6. The method of claim 5, wherein said cultured adipocytes are incubated with a SUR1 agonist in the presence and absence of said compound.

7. The method of claim 5, wherein the lipogenic marker is selected from the group consisting of $Ca^{2+}$ influx, FAS activity, GPDH activity and triglyceride accumulation.

8. The method of claim 5, wherein said anti-lipolytic marker is glycerol release into the culture medium or increased intracellular cAMP levels.

* * * * *